US00PP21030P3

(12) United States Plant Patent
Tsechelidis

(10) Patent No.: US PP21,030 P3
(45) Date of Patent: Jun. 1, 2010

(54) KIWI PLANT NAMED 'TSECHELIDIS'

(50) Latin Name: *Actinidia deliciosa*
Varietal Denomination: Tsechelidis

(75) Inventor: Christos Tsechelidis, Episkopi Anthemion Imathia (GR)

(73) Assignee: Karipidis L. -Tsechilidou E. S.P., Naoussa (GR)

( * ) Notice: Subject to any disclaimer, the term of this patent is extended or adjusted under 35 U.S.C. 154(b) by 24 days.

(21) Appl. No.: 11/987,178

(22) Filed: Nov. 28, 2007

(65) Prior Publication Data

US 2009/0138997 P1 May 28, 2009

(51) Int. Cl.
*A01H 5/00* (2006.01)

(52) U.S. Cl. ..... Plt./156

(58) Field of Classification Search ..... Plt./156
See application file for complete search history.

(56) References Cited

OTHER PUBLICATIONS

Huang, et al. Microsatellite DNA in *Actinidia chinensis*: isolation, characterisation, and homology in related species, Theor Appl Genet (1998) 97: 1269-1278.

Korkovelos, et al., Effectiveness of SSR molecular markers in evaluating the phylogenetic relationships among eight *Actinidia* species, Scientia Horticulturae 116 (2008) 305-310.

Korkovelos, et al., Screening Microsatellites for their Effectiveness to Identify and Differentiate among *Actinidia* Genotypes, Proc. IS on Kiwifruit, Ed. H. Huang, Acta Hort 610, ISHS pp. 357-363, 2007.

*Primary Examiner*—Annette H Para
(74) *Attorney, Agent, or Firm*—Andreas Baltatzis; Kramer & Amado, P.C.

(57) ABSTRACT

A new and distinctive variety of the kiwi plant, *Actinidia deliciosa*, named 'Tsechelidis' is described. The new variety is characterized by very large oblong fruit covered with downy hairs, and very broad ovate leaves having acuminate apexes, among other features. The size and uniformity of the fruit provide significantly higher yield than other known varieties of kiwi.

9 Drawing Sheets

Latin name of the genus and species of the plant claimed: *Actinidia deliciosa.*

Variety denomination: 'Tsechelidis'.

BACKGROUND OF THE INVENTION

Kiwi plants have been cultivated outside their native China for over one hundred years. Known varieties or cultivars include Hayward, Meteor, Hort16A, Abbott, Tomua, Jade Moon, Bruno, Monty, Matua and Kuimi. Hayward is the most popular variety worldwide. Kiwi plants are now commercially grown in New Zealand, Italy, Chile, France, Greece, Japan, China and the United States.

Kiwi plants are commercially grown for their oblong or oval fruit, having brown skin covered in short hairs. The flesh, firm until fully ripe, is glistening, bright green or sometimes yellow, brownish or off-white, except for the white, succulent center from which radiate many fine, pale lines. Between these lines are scattered minute dark-purple or nearly black seeds, unnoticeable in eating.

Kiwi plants may be propagated by seed, grafting or cutting.

SUMMARY OF THE INVENTION

The present invention relates to a new and distinctive kiwi variety characterized by very large, oblong fruit covered with downy hairs, and very broad ovate leaves having acuminate apexes, among other features. The size and uniformity of the fruit provide significantly higher yield than other known varieties of kiwi. The new variety designated 'Tsechelidis' was derived from the 'Hayward' variety in Episkopi, Imathia, Greece and has been asexually reproduced by cutting, among other methods.

'Tsechelidis' is further distinguished by the nutritional characteristics of the fruit as well as the qualitative characteristics. Furthermore, a molecular genetic analysis distinguishes 'Tsechelidis' from 'Hayward' as indicated by several polymorphisms in known alleles.

BRIEF DESCRIPTION OF THE PHOTOGRAPHS

The accompanying color photographs of 'Tsechelidis' show the new variety as well as comparisons of the 'Tsechelidis' variety to the 'Hayward' variety.

DETAILED DESCRIPTION OF THE INVENTION

Figure 1:
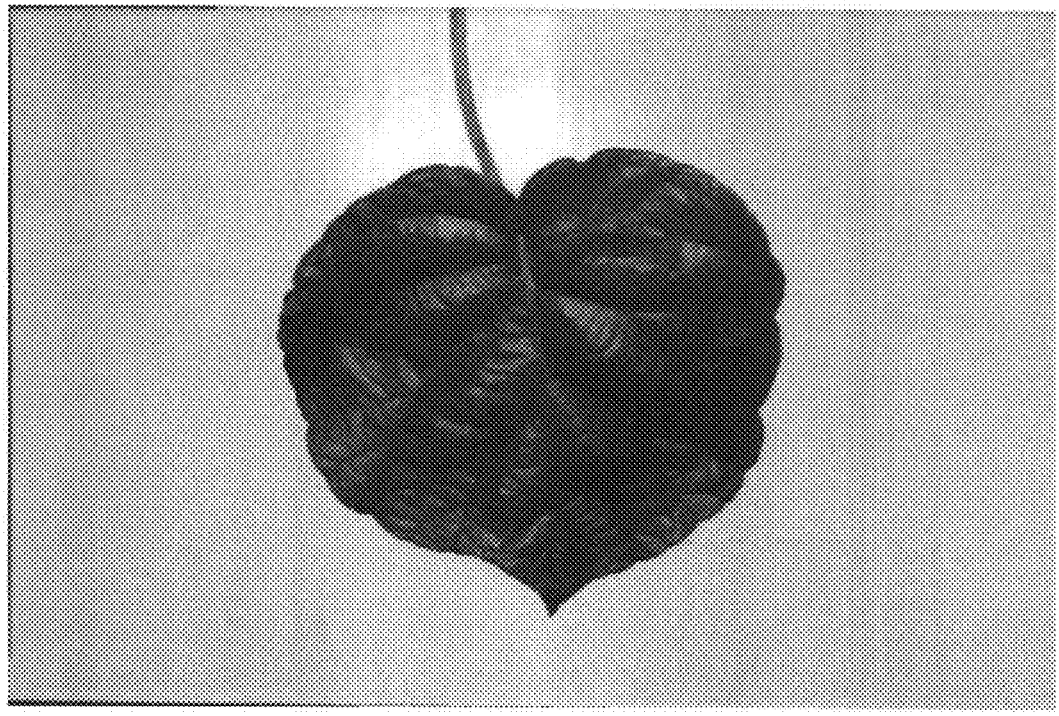
FIG. 1 shows a typical leaf of 'Tsechelidis'.
Figure 2:
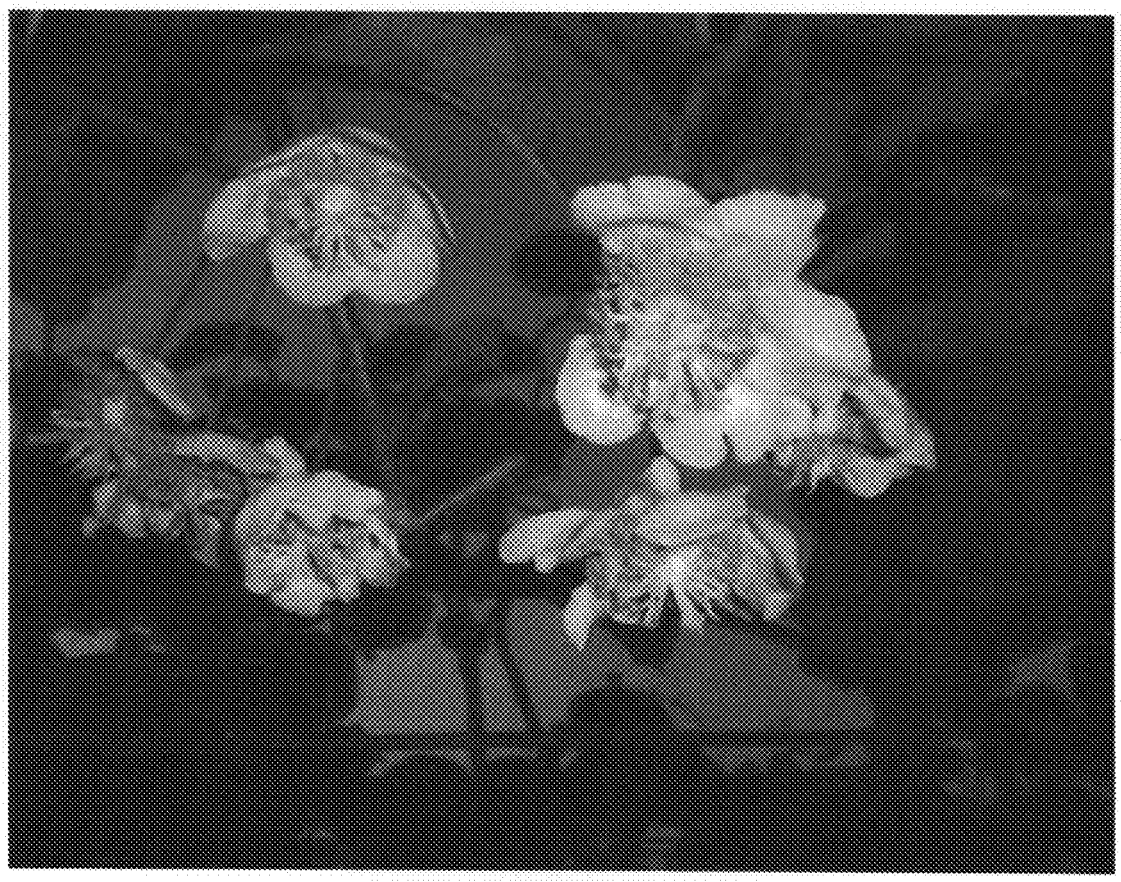
FIG. 2 shows typical flowers of 'Tsechelidis'.
Figure 3:
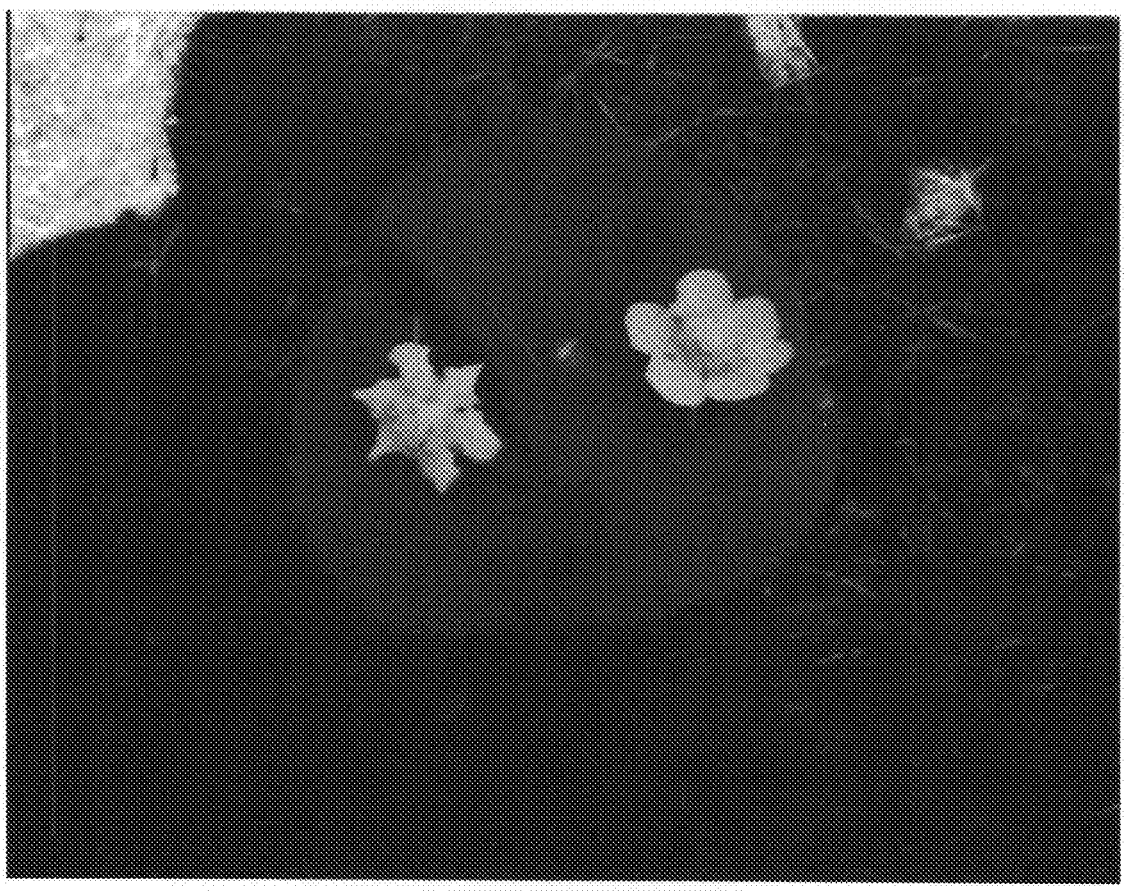
FIG. 3 shows a typical flower of 'Tsechelidis' as compared to a typical flower of 'Hayward'.
Figure 4:
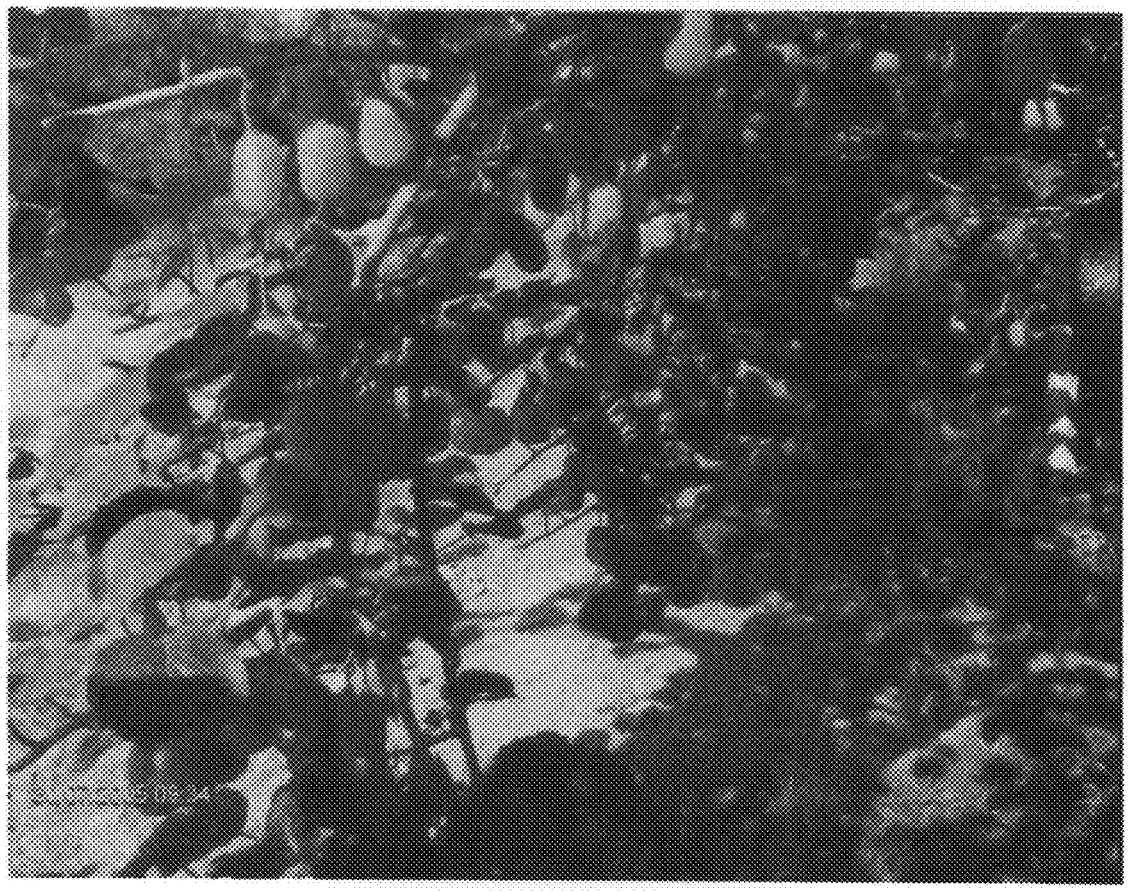
FIG. 4 shows typical fruit of 'Tsechelidis' on the vine.
Figure 5:
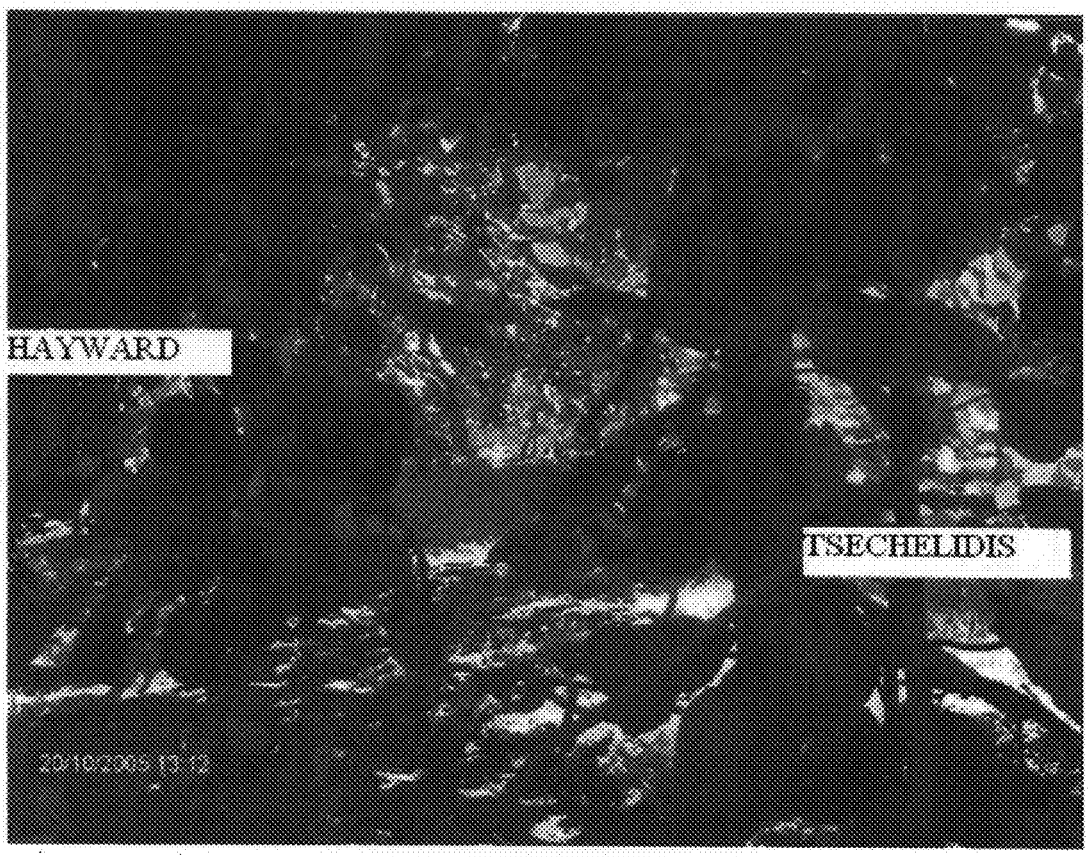
FIG. 5 shows typical fruit of 'Tsechelidis' on the vine as compared to typical fruit of 'Hayward' on the vine.
Figure 6:
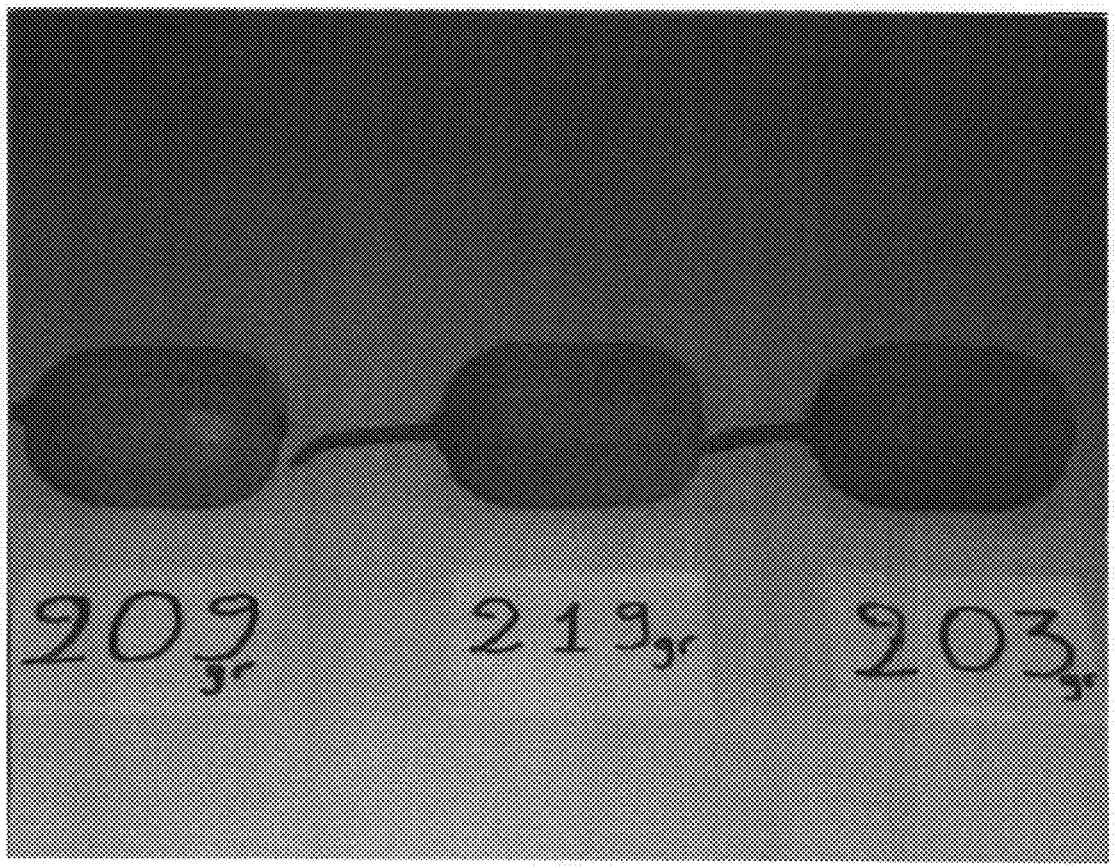
FIG. 6 shows typical fruit of 'Tsechelidis' with stems attached.
Figure 7:
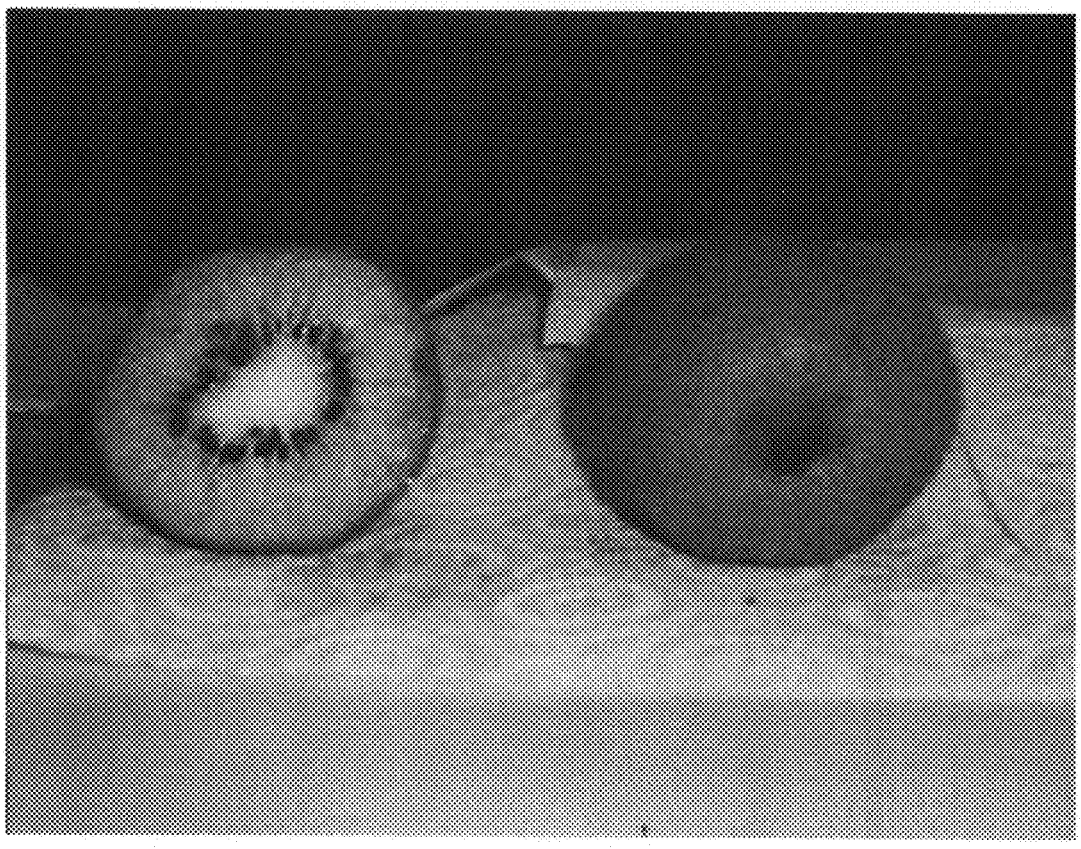
FIG. 7 shows a cross-section and a stylar end view of a typical fruit of 'Tsechelidis'
Figure 8:
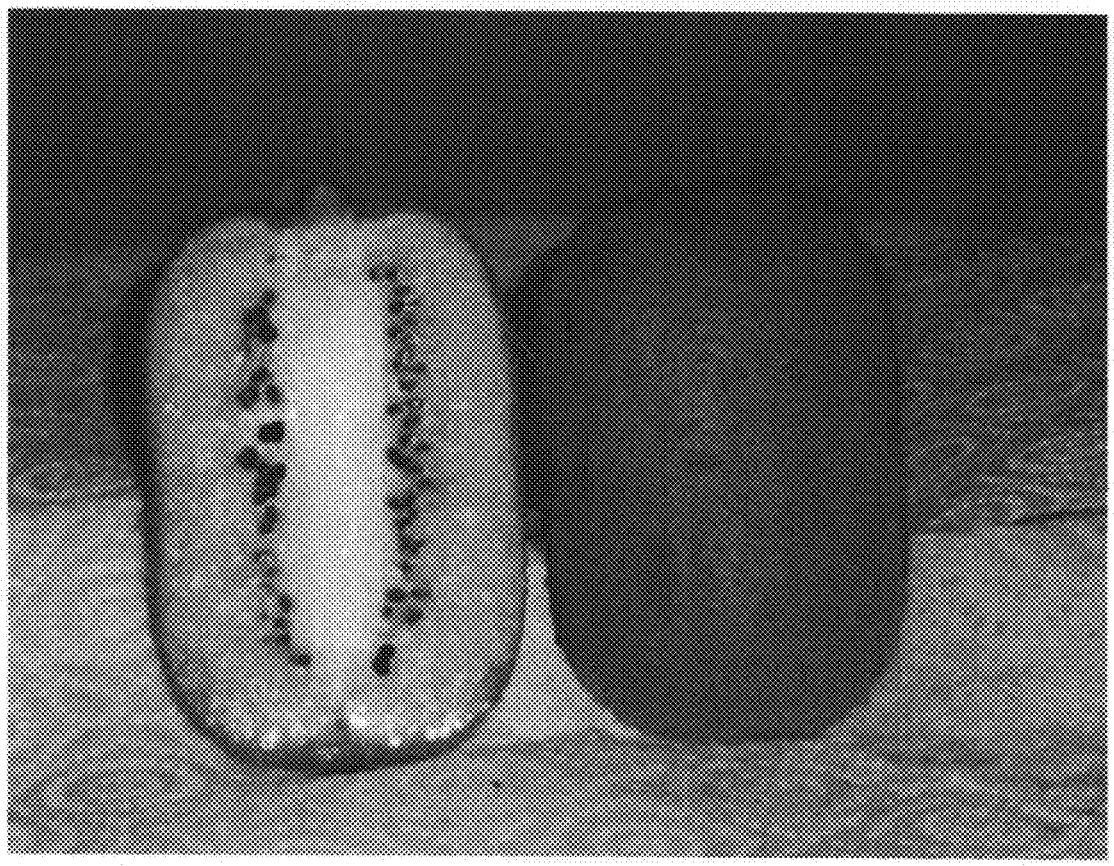
FIG. 8 shows a cross-section and a side view of a typical fruit of 'Tsechelidis'.
Figure 9:
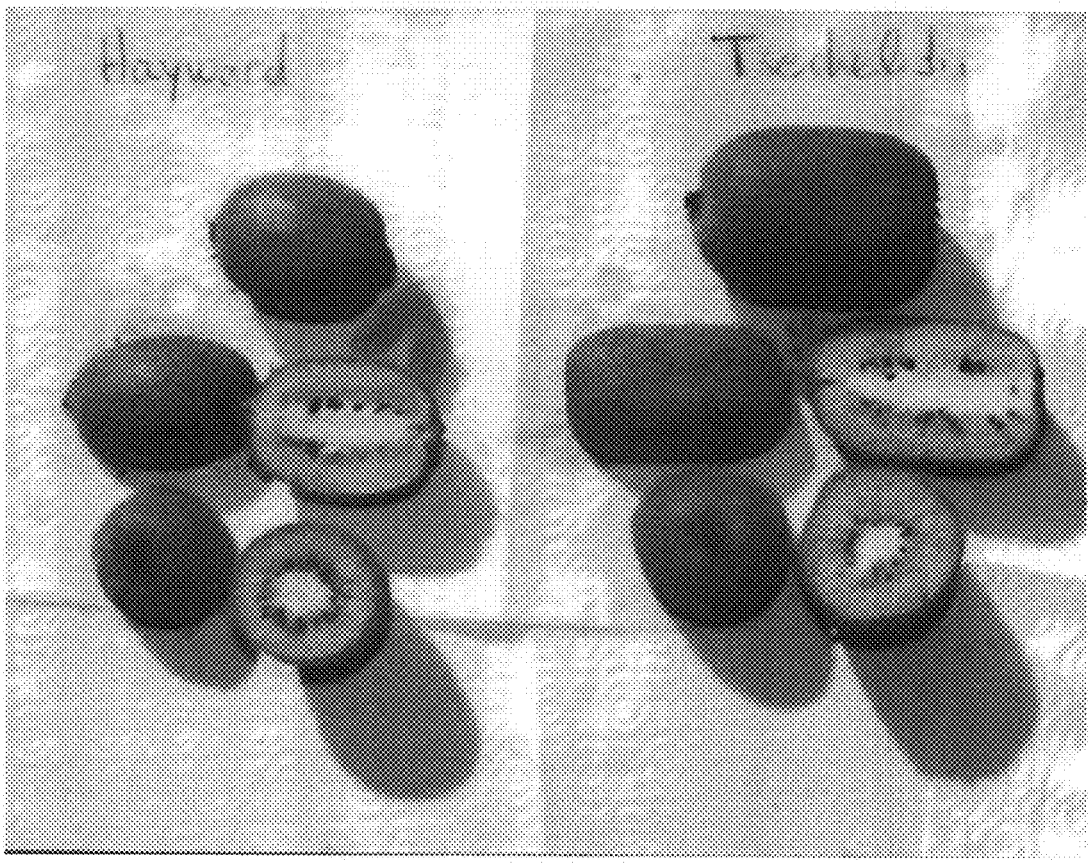
FIG. 9 shows typical fruit of 'Tscehelidis' as compared to typical fruit of 'Hayward'.

The present invention is a new and distinct variety of *Actinidia deliciosa* plants having the several characteristics that distinguish the variety from other kiwi plants, particularly the 'Hayward' variety.

The new variety 'Tsechelidis' was discovered in Episkopi, Imathia, Greece, when the inventor planted seeds from selected Hayward plants with the purpose of obtaining a group of male plants. From this original group of twenty plants, a single plant was identified as female. During its first harvest in 1994, the female plant bore unusually large fruit as compared to plants of the 'Hayward' variety. The female plant was monitored for the next two harvests and consistently bore the unusually large fruit, as well as other features which distinguished it from 'Hayward'. The female plant was then used to propagate the 'Tseehelidis' variety by asexual reproduction beginning in 1996.

The 'Tsechelidis' variety has been continuously asexually reproduced by cuttings from 1996 through 2007. The distinguishing characteristics of the variety continue to run true in the propagated plants, as shown by about 1000 plants covering ½ hectare. Furthermore, no changes have appeared in the new variety when grafted on 'Hayward'. In addition to cuttings, the new variety can be asexually reproduced by grafting to rootstocks of *A. deliciosa*.

Male pollenizers suitable for 'Tsechelidis' may include, but are not limited to, 'Mania'. At this time the 'Tsechelidis' variety is being tested for self-pollenization by the University of Volvos, Greece. According to preliminary results, 'Tsechelidis' is characterized by up to 75% self-pollenization as compared to 2% for 'Hayward'.

'Tsechelidis' should be cultivated in areas that are not affected by spring frost. Temperatures of less than −2° C. will damage the tender shoots of the plant and suspending growth or reduce the setting process. Also, frost in early autumn to late October may damage fruit situated on the vine. The presence of strong wind, particularly in May, may result in considerable decrease of flowers borne by the plant.

Distinguishing Characteristics from Known Varieties

The following is a comparison of the fruit production an orchard of 'Tsechelidis' as compared with cultivated 'Hayward' situated in the area of Episkopi-Anthemion in the prefecture of Imathia, Greece. At the time of this study (2006) the 'Tsechelidis' orchard was five years old.

The listed observations, measurements and assessments were made in the following categories:

1. Plant and fruit characteristics
2. Quantitative production data (yield, number of fruits/plants and average fruit weight).
3. Level of nutritional elements in leaves and fruit.
4. Qualitative fruit characteristics (resistance to pressure, pH, soluble solids (° Brix), vitamin C, acids, sugars, Thiault index and dry matter).
5. Plant/Fruit disease and pest resistance/susceptibility 1. Plant and Fruit Characteristics:

The chart below describes the physical differences between 'Tsechelidis' and the known 'Hayward' variety. The Horticultural terminology applied below is used in accordance with revised UPOV guidelines for kiwi (Test Guidelines—TG/98/6 —*Actinidia* 2001-04-04, available at http://www.upov.int/en/publications/tg-rom/tg098/tg_98_6. pdf).

TABLE 1

| UPOV Characteristics for comparison of varieties | 'HAYWARD' | 'TSECHELIDIS' |
|---|---|---|
| Plant: vigor | Medium | Strong |
| Leaf blade: shape | Broad ovate | Very broad ovate |
| Leaf blade: shape of apex | Acute | Acuminate |
| Leaf blade: green color of upper side | Medium | Dark |
| Petal: curvature of apex | Strongly expressed | Very strongly expressed |
| Fruit: size | Large | Very large |
| Fruit: general shape | Ellipsoid | Oblong |
| Fruit: general shape of stylar end | Flat | Between slightly depressed and flat |
| Fruit: shape of shoulder at stalk end | Rounded | Squared |
| Fruit: type of hairiness | Hirsute | Downy |
| Time of beginning of flowering | Late | Medium |

The shoots of 'Tsechelidis' grow more vigorously than 'Hayward', though there is no difference with respect to resilience against pest and diseases. The fruits of 'Tsechelidis' are more oblong than 'Hayward' (the ratio of fruit length/width is 1.41 and 1.24 respectively). Furthermore, the fruits of 'Tsechelidis' are larger and more uniform in size. 'Tsechelidis' do no require thinning absent defective fruit, unlike 'Hayward'. Additionally, due to the larger fruit size, any decrease that may be caused by low temperatures during the flowering season or poor pollination of the fruits will not affect the marketability of the fruits, in contrast with 'Hayward'.

In addition to the distinguishing features between 'Tsechelidis' and 'Hayward' listed above, the following characteristics were identified by the European Community Plant Variety Office (CPVO). Again the terminology is presented according to the revised UPOV guidelines for kiwi (Test Guidelines—TG/98/6—*Actinidia* 2001-04-04, available at http://www.upov.int/en/publications/tg-rom/tg098/tg_98_6.pdf). The UPOV characteristics are botanical terms known in the art for description plant varieties.

TABLE 2

| UPOV No. | Characteristics | State of Expression |
|---|---|---|
| 5 | Young shoot: Hairiness | present |
| 6 | Young shoot: Density of hair | medium |
| 7 | Young shoot: Type of hairiness | hirsute |
| 8 | Young shoot: Anthocyanin coloration of growing tip | medium |
| 9 | Stem: Thickness | medium |
| 11 | Stem: Roughness of bark | medium-rough |
| 12 | Stem: Hairiness | present |
| 13 | Stem: Density of hair | medium |
| 14 | Stem: Type of hairiness | bristly |
| 15 | Stem: Size of lenticels | medium |
| 16 | Stem: Number of lenticels | medium |
| 19 | Stem: Size of bud support | small to medium |
| 20 | Stem: Profile of proximal face of bud support (if sloping) | convex |
| 21 | Stem: Presence of bud cover | present |
| 22 | Stem: Size of hole in bud cover | medium |
| 23 | Stem: Leaf sear | shallow |
| 26 | Leaf blade: Shape | very broad ovate |
| 27 | Leaf blade: Shape of apex | acuminate |
| 28 | Leaf blade: Arrangement of basal lobes | slightly apart |
| 29 | Leaf blade: Hair on upper side | medium |
| 30 | Leaf blade: Hair on lower side | medium |
| 31 | Leaf blade: Puckering/Blistering on upper side | medium |

TABLE 2-continued

| UPOV No. | Characteristics | State of Expression |
|---|---|---|
| 34 | Leaf blade: Presence of variegation | absent |
| 37 | Leaf: Ratio petiole length/blade length | large |
| 38 | Petiole: Density of hair | medium-dense |
| 39 | Petiole: Anthocyanin coloration on tipper side | medium |
| 40 | Flower bud: anthocyanin coloration of protruding petal end | medium |
| 41 | Inflorescence: Predominant number of flowers | one |
| 42 | Flower stalk: Length | medium-long |
| 43 | Flower stalk: Density of hair | medium |
| 44 | Flower stalk: Length of hair | medium |
| 45 | Flower: Number of sepals | 6 |
| 47 | Sepal: Density of hair | sparse |
| 48 | Sepal: Length of hair | medium-short |
| 49 | Flower: Diameter | very large |
| 50 | Flower: Arrangement of petals (viewed from beneath) | overlapping |
| 51 | Petal: Curvature of apex | strongly expressed |
| 52 | Petal: Type of coloration (adaxial side) | single colored |
| 54 | Petal: Different shades of color | absent |
| 60 | Styles: Number | many |
| 62 | Styles: Attitude | erect and horizontal |
| 63 | Fruit: Size | very large |
| 64 | Fruit: General shape | oblong |
| 65 | Fruit: Shape in cross-section (at median) | elliptic |
| 66 | Fruit: General shape at stylar end | slight depressed and flat |
| 67 | Fruit: Presence of calyx ring | weakly expressed |
| 68 | Fruit: Shape of shoulder at stalk end | squared |
| 69 | Fruit: Length of stalk | long |
| 70 | Fruit: Ratio stalk length/fruit length | large |
| 71 | Fruit: Persistence of sepals | present |
| 72 | Fruit: Conspicuousness of lenticels on skin | inconspicuous |
| 74 | Fruit: Hairiness of skin | present |
| 75 | Fruit: Density of hair | medium |
| 76 | Fruit: Type of hairiness | downy |
| 77 | Fruit: Distribution of hairs | evenly spread |
| 79 | Fruit: Adherence of hair to skin (when rubbed) | medium-strong |
| 84 | Fruit: Diameter of core relative to fruit | medium to large |
| 85 | Fruit: General shape of core (in cross section) | transverse elliptic |
| 86 | Fruit: Fluting of core (in cross section) | present |
| 88 | Fruit: Sweetness | medium-low |
| 89 | Fruit: Acidity | medium |
| 90 | Time of vegetative bud burst | medium |
| 91 | Time of beginning flowering | medium-late |
| 92 | Time of maturity for harvest | medium-late |

In addition to the above listed characteristics set forth according to the UPOV guidelines, the following measurements are typical of 'Tsehedilids.' The typical size of the leaves includes a stalk length of 12–14 cm, a length from stalk to apex of 18–20 cm and a leaf width of 16-18 cm. The typical flower diameter is 5–7 cm. The flowers are typically characterized by 5-6 sepals, 6-8 petals and 35-45 styles. The stalk length of the flowers typically ranges from 6–9 cm.

With regards to the fruit, the fruit length typically averages about 7.96 cm. The fruit width typically ranges from about 5.15 cm (small width) to about 5.71 cm (large width). The fruit weight typically ranges from 150-170 g.

The following color description has been provided according to the R.H.S. Colour Chart.

TABLE 3

| Characteristic Botanical Features | Color according to RHS Colour Chart |
|---|---|
| Stem: Color of shoot on sunny side | 178A-Greyed-Red Group |
| Stem: Color of lenticels | 177C-Greyed-Orange Group |
| Leaf blade: Color of upper side | 137B-Green Group |
| Leaf blade: Color of lower side | 146C-Yellow-Green Group |
| Sepal: General color | 200D-Brown Group |
| Petal: Main color on adaxial side | 155D-White Group |
| Filament: Color | 155C-White Group |
| Anther: Color | 13C-Yellow Group |
| Styles: Color | 158B-Yellow-White Group |
| Fruit: Color of skin | 199A-Grey-Brown Group |
| Fruit: Color of hairs | 199D-Grey-Brown Group |
| Fruit: Color of skin at maturity for consumption | 199A-GreyBrown Group |
| Fruit: Color of outer pericarp | 141C-Green Group |
| Fruit: Color of inner pericarp | 141C-Green Group |
| Fruit: Color of core | 157D-Green-White Group |

2. Quantitative Production Data:

TABLE 4

| Parameter | 'TSECHELIDIS' | 'HAYWARD' | Significance level (P) |
|---|---|---|---|
| Total number of fruits/plant | 250 | 279 | P > 0.05 |
| Number of marketable fruits | 249 | 222 | P > 0.05 |
| Rate of marketable fruits (%) | 99.6 | 79.6 | — |
| Total yield (kg/plant) | 41.9 | 29.9 | P > 0.05 |
| Yield of marketable fruits (kg/plant) | 41.6 | 25.1 | 0.001 < P < 0.01 |
| Yield of marketable fruits (%) | 99.3 | 83.9 | — |
| Average weight of marketable fruits (g) | 167.0 | 114.5 | P < 0.001 |
| Average weight of non-marketable fruits (g) | 237.0 | 88.8 | P > 0.001 |

P > 0.05 signifies a statistically insignificant difference.

'Tsechelidis' has a greater density of buds in each stem than 'Hayward', whereby each stem, which has 13 buds, produces about 10 kg of fruit. Therefore, each 'Tsechelidis' tree, having about 15-18 stems, yields about 140-150 kg of fruit. The high yield, and large size and uniformity of the fruit of 'Tsechelidis', as compared to the 'Hayward', are significant advantages, particularly with regard to reducing production costs. This data was taken during a harvest affected by adverse weather during the growing season in Imathia, Greece.

3. Level of Nutritional Elements The following is table that shows the statistically significant differences in nutritional elements between 'Tsechelidis' and 'Hayward'.

TABLE 5

| Parameter | 'TSECHELIDIS' | 'HAYWARD' |
|---|---|---|
| Leaves: nitrogen level | 1.95% | 2.53% |
| Fruit skin: phosphorus | 0.13% | 0.08% |
| Fruit skin: potassium | 2.35% 1.95% | |
| Fruit skin: magnesium | 0.08% | 0.06% |
| Fruit skin: manganese | 12.6 ppm | 8.0 ppm |
| Fruit flesh: nitrogen | 0.76% 0.95% | |
| Fruit flesh: phosphorus | 0.13% | 0.16% |
| Fruit flesh: manganese | 10.3 ppm | 6.2 ppm |
| Fruit flesh: copper | 6.79 ppm | 10.51 ppm |
| Fruit flesh: proportion of N/Ca | 2.30 | 2.71 |

4. Qualitative fruit characteristics The following tables show specific qualitative fruit characteristics between 'Tsechelidis' and 'Hayward'. The first table lists measurements of fruit immediately after harvest. The second table lists measurements taken of fruit held in refrigerated storage for two months after harvest.

TABLE 6

| Parameter | 'TSECHELIDIS' | 'HAYWARD' | Significance level (P) |
|---|---|---|---|
| Measurements Taken During Harvest | | | |
| Resistance to pressure (lb/in$^2$) | 23.0 | 27.0 | 0.001 < P < 0.01 |
| Flesh pH | 3.34 | 3.25 | 0.01 < P < 0.05 |
| Soluble solids (°Brix)(%) | 7.30 | 6.70 | P > 0.05 |
| Vitamin C (mg/100 g fresh weight) | 79.2 | 37.8 | P < 0.001 |
| Measurements Taken During Harvest | | | |
| Malic acid (g/l) | 4.5 | 4.0 | P > 0.05 |
| Sugars (g/l) | 62.8 | 57.2 | 0.01 < P < 0.05 |
| Thiault index | 107.7 | 97.6 | 0.01 < P < 0.05 |
| Dry matter (%) | 15.30 | 15.82 | P > 0.05 |

TABLE 7

| Measurements Taken Two (2) Months After Harvest | | | |
|---|---|---|---|
| Parameter | 'TSECHELIDIS' | 'HAYWARD' | Significance level (P) |
| Resistance to pressure (lb/in$^2$) | 10. | 10.9 | P > 0.05 |
| Flesh pH | 3.32 | 3.41 | P < 0.001 |
| Soluble solids (°Brix) (%) | 13.6 | 13.0 | P > 0.05 |
| Vitamin C (mg/100 g fresh weight) | 80.2 | 38.3 | P < 0.001 |
| Malic acid (g/l) | 4.8 | 4.5 | P > 0.05 |
| Sugars (g/l) | 84.4 | 80.0 | P > 0.05 |
| Thiault index | 132.4 | 125.0 | P > 0.05 |

Based on the above information, the following distinctions may be drawn between 'Tsechelidis' and 'Hayward'. The fruit of 'Tsechelidis' ripen 7-10 days earlier than 'Hayward', which is shown by the fruit's lower resistance to pressure and their slight superiority in soluble solids (° Brix) during harvest. Despite the earlier ripening, the resistance to pressure of 'Tsechelidis' after two months of refrigerated storage was the same as 'Hayward'.

5. Plant/fruit disease and pest resistance/susceptibility

There is no difference between 'Tsechelidis' and 'Hayward' with respect to resilience against pest and diseases. There are no other observed characteristics specific to plant/fruit disease and pest resistance/susceptibility.

Molecular Genetic Analysis

A molecular genetic analysis was conducted by Dr. Athanasios Mavromatis, Professor of Genetics & Plant Breeding (University of Thessaly, School of Agricultural Services) comparing 'Tsechelidis' with 'Hayward' based on known microsatellite DNA markers using PCR. The method is recognized as an accurate and repeatable molecular analysis for *Actinidia*. Huang, W.G., Cipriani, G., Morgante, M., Testolin, R. (1998) Microsatellite DNA in *Actinidia chinensis*: isolation, characterization, and homology in related species. Theor. Appl. Genet. 97 (8): 1269-1278.

The DNA analysis was performed as follows: Repeatable samples of four genotypes were used (commercial clones of 'Hayward' (one female, one male) and 'Tsechelidis' (one female, one male)). Leaf samples of 0.3 g per genotype was used for DNA extraction process according to a modified cetyltrimethylammonium bromide (CTAB) method. The extract DNA was quantified on agarose gel by comparison with report samples (DNA marker). The DNA quality and quantity was tested to ensure accuracy of the molecular genetic analysis.

Thirteen known primer pairs were used for amplifying dinucleotide tandems AG/CT and AC/GT. The primer pairs used were: UDK 96-022, UDK 97-402, UDK 99-152, UDK 96-053, UDK 97-411, UDK 96-030, UDK 96-001, UDK 96-037, UDK 96-034. UDK 99-168, UDK 96- 092, UDK 97-406 and UDK 97-407. The primers were developed in a bilateral European Union International Cooperation with Developing Countries (INCO-DC) project performed by University of Udine, Italy; Chinese Agricultural University, Beijing China; INRA, France; and University of Thessaly, Greece.

The sequence of all of the list primers are known and published the prior art. For example the sequences of UDK 96-001, UDK 96-022, UDK 96-030, UDK 96-034, UDK 96-037, UDK 97-402, UDK 97-406, UDK 97-407 and UDK-41 1 are all published in Huang et al., Microsatellite DNA in *Actinidia chinesis*: isolation, characterization, and homology in related species. Theor. Appl. Genet. (1998) 97: 1269-1278. UDK 96-037 a and b listed below indicate the two polymorphic loci amplified in the same gel for the same primer UDK 96-037. The sequences of UDK 96-053 and UDK 99-152 are published in Korkovelos et al. Effectiveness of SSR molecular markers in evaluating the phylogenetic relationships among eight *Actinidia* species. Scientica Horticulturae 116 (2008) 305-310. UDK 96-092 and UDK 99-168 are also know primers as disclosed by Korkovelos et al. Screening microsatellites for their effectiveness to identify and differentiate among *Actinidia Genotypes*. Acta Hort. 610 (2003) 357-363.

The PCR products were separated in 6% polyacrylamide gels 1.5 mm thick. Band visualization was made with silver nitrate. The results of the study indicated that at least seven out of 13 primer pairs were polymorphic. Therefore, the study provides grounds for distinguishing between genetic material from 'Tsechelidis' as compared to 'Hayward'.

The polymorphic primer pairs are described in the table below according to the presence and absence of alleles of the same molecular weight.

TABLE 8

| DNA primer/alleles | 'TSECHELIDIS' | 'HAYWARD' |
|---|---|---|
| 99-152 | | |
| 97-411 | + | − |
| 96-030 | | |
| 96-037a | − | + |
| 96-037b | + | − |
| 96-034 | + | − |
| 96-092 | + | − |
| 97-406 | − | + |

The genetic difference confirmed through diverse binding patterns indicate that the 'Tsechelidis' variety is genetically distinct from 'Hayward'.

What is claimed is:

1. A new and distinct variety of *Actinidia deliciosa* plant named 'Tseehelidis' substantially as shown and described.

* * * * *

UNITED STATES PATENT AND TRADEMARK OFFICE

CERTIFICATE OF CORRECTION

PATENT NO. : PP 21,030 P3
APPLICATION NO. : 11/987178
DATED : June 1, 2010
INVENTOR(S) : Christos Tsechelidis It is certified that error appears in the above-identified patent and that said Letters Patent is hereby corrected as shown below:

In Col. 3, Line 29, replace but are not limited to, 'Mania'. At this time the 'Tsechelidis' with -- but are not limited to, 'Matua'. At this time the 'Tsechelidis' --

Signed and Sealed this

Twenty-ninth Day of June, 2010

David J. Kappos

David J. Kappos
*Director of the United States Patent and Trademark Office*